United States Patent [19]

Edmunds

[11] Patent Number: 4,767,411
[45] Date of Patent: Aug. 30, 1988

[54] PROTECTIVE CATHETER SLEEVE

[76] Inventor: L. Henry Edmunds, 130 N. Roberts Rd., Bryn Mawr, Pa. 19010

[21] Appl. No.: 72,913

[22] Filed: Jul. 14, 1987

[51] Int. Cl.$^4$ .............................................. A61M 5/18
[52] U.S. Cl. ............................ 604/180; 128/DIG. 26
[58] Field of Search ................. 128/DIG. 26; 604/86, 604/180, 174, 178, 179

[56] References Cited

U.S. PATENT DOCUMENTS

| | | |
|---|---|---|
| 3,683,911 | 8/1972 | McCormick . |
| 3,782,377 | 1/1974 | Rychlik . |
| 3,900,026 | 8/1975 | Wagner . |
| 4,397,641 | 8/1983 | Jacobs . |
| 4,453,100 | 9/1985 | Brodsky . |
| 4,484,914 | 11/1984 | Brown . |
| 4,519,793 | 5/1985 | Galindo . |
| 4,534,762 | 8/1985 | Heyer . |
| 4,645,492 | 2/1987 | Weeks . |

*Primary Examiner*—Carroll B. Dority, Jr.
*Attorney, Agent, or Firm*—Merchant, Gould, Smith, Edell, Welter & Schmidt

[57] ABSTRACT

A protective catheter sleeve (12) for use with indwelling catheters, wires and the like, such as during long-term patient care, includes a surrounding flexible side wall (14), the upper end of which is adhesively secured about the catheter and the lower end of which is adhesively secured about the puncture site on the patient skin, to define a sealed chamber therein. A needle access port (38) is provided in the side wall (14) for replenishing/removing antiseptic fluid therein as necessary to minimize the chances of infection. A second embodiment (50) includes a resealable seam (52, 54) in the side wall to facilitate removal/replace ment of the protective catheter sleeve around an indwelling, transcutaneous catheter or other device without disturbing the sleeve.

17 Claims, 2 Drawing Sheets

PROTECTIVE CATHETER SLEEVE

TECHNICAL FIELD

The present invention relates generally to medical devices. More particularly, this invention concerns a protective catheter sleeve for providing a sterile fluid seal at the site of an in-dwelling transcutaneous catheter whereby the antiseptic fluid can be sampled, replenished or changed as necessary without disturbing the catheter or sleeve to help avoid infection and other complications, especially in long-term applications.

Background Art

Modern medicine requires long-term, transcutaneous catheter access to the vascular system of a patient for infusion of drugs and nutrients, analysis of blood constituents, and support of circulation. Such transcutaneous catheters are required in many medical applications, including diagnosis and treatment, and are being used for increasingly longer terms. These catheters provide access for the administration of drugs, including anesthetics, and drainage of fluid for analysis or disposal. Transcutaneous tubes and wires are required to power and control the artificial heart and are likely to be needed for the development of other artificial internal organs.

Catheter infection, defined as the entrance of microorganisms at the puncture site around any transcutaneous catheter, tube, wire, or other foreign body, is a serious complication which limits the long-term use of such devices. Microorganisms invariably gain access to the tract of the catheter, tube or wire at the skin surface and grow inwards around the catheter tract to reach the vascular system. This can result in severe infection that invariably requires removal of the catheter or foreign body in the infected catheter tract. The incidence of infection is directly proportional to the duration a catheter is maintained at a particular site.

Attempts to prevent catheter tract infections have heretofore been unreliable and unsuccessful. Basically, surgical methods involve construction of long and/or tortuous subcutaneous tracts between the skin opening and the body cavity, organ or vessel. Examples of this include Techoff, peritoneal dialysis catheters wherein a subcutaneous prosthetic cuff is used to stabilize the catheter as it crosses the skin barrier and the long transcutaneous tunnels used for power and control lines of the Jarvik artificial heart.

Catheters placed in blood vessels, lymph channels, and the central nervous system cannot now be maintained indefinitely because of the risk of septicemia and meningitis. These catheters can be safely maintained with assiduous nursing care for 48-96 hours and then must be changed or removed. Occasionally, Venous catheters used for long-term nutrition can be maintained for longer periods by expensive and arduous nursing procedures. However, despite these procedures infection occurs in approximately 5% of patients who require intravenous nutrition for more than a few days.

The mechanism by which transcutaneous catheters, tubes, and wires lead invariably to infection is as follows. Microorganisms, including bacteria, fungi and viruses are ubiquitous in our environment. Even after extensive skin sterilization using bactericidal and fungicidal chemicals, microorganisms can contaminate the skin surface from the air or hair follicles. If the skin barrier is broken and prevented from repair and restoration by a transcutaneous catheter or other foreign body, microorganisms can gain entrance along the catheter to the interior of the body. Thus it is not possible to maintain sterility around the skin site of entrance of any foreign body or catheter indefinitely by methods presently available.

The entrance of microorganisms into the body and the penetration site is facilitated by small movements of the catheter in and out as the patient moves and breaths. It is not possible to stabilize any catheter or other transcutaneous device so that small movements at the skin are completely prevented. Thus microorganisms at the penetration site are invariably carried by catheter movements beneath the skin into the body along the catheter tract.

Various devices have been available heretofore for retaining or stabilizing such catheters in place. For example, U.S. Pat. Nos. 4,534,762 to Heyer, 4,484,914 to Brown, and 4,519,793 to Galindo are representative of the prior art in this regard. However, these devices are neither adapted nor intended to prevent entrance of microorganisms along the catheter tract. These devices are designed to prevent dislodgement of catheters, needles and other transcutaneous devices from the internal vessel, cavity or organ when the patient moves, or when the catheter or site of entrance is disturbed.

There have been some prior attempts to prevent infection along catheters. For example, U.S. Pat. No. 3,683,911 to McCormick describes an adhesive patch with a sleeve that encircles the catheter and stabilizes it in relation to the skin. The patch and sleeve are designed to be impervious to bacteria, and the skin adhesive contains an unidentified antibacteridal chemical. This device does not provide a means for continuous application of varied and effective antiseptic solutions, nor does it provide means for identifying contaminating microorganisms nor for changing the antiseptic chemicals insitu. Thus the McCormick device is of limited effectivity because no one antiseptic is universally effective against all types of microorganisms.

U.S. Pat. No. 3,782,377 to Rychlik shows a protective shield that is placed over the skin puncture site of a needle or catheter. This cup-like shield contains a "disinfectant" held within a wick or sponge which is placed over the catheter and puncture site and held to the skin by surrounding adhesive. This device fails to completely surround the catheter puncture site and adjacent catheter in that the catheter exits beneath the protective cup laterally. Microorganisms emerging from hair follicles cannot be prevented from accessing the puncture site. Morever, microorganisms can pass along the catheter as it emerges beneath the cup and surrounding adhesive strip. Lastly, the 'disinfectant' cannot be cultured, inspected, analyzed, renewed or varied. Thus resistant organisms that are not killed or inhibited by the disinfectant, can gain access to the puncture site.

A need has thus arisen for an improved protective catheter sleeve that provides a continuous fluid seal about the puncture site, which can be sampled, cultured, analyzed, replenished, and filled as necessary without disturbing the sleeve or catheter.

SUMMARY OF THE INVENTION

The present invention comprises a protective catheter sleeve which overcomes the foregoing and other problems associated with the prior art. In accordance with the invention, there is provided a protective catheter sleeve which is adapted to define a sealed chamber of antiseptic fluid between the catheter and the patients skin to minimize or prevent infection, particularly with in-dwelling catheters which are left in place for extended periods. Two embodiments are disclosed. In the first embodiment, the sleeve comprises a surrounding wall with a closed top end and an open bottom end. The bottom end includes a peripheral flange for adhesive connection to the skin. This adhesive flange surrounds the catheter, wire or foreign body and the skin puncture site. The top end is secured to the catheter, such as by adhesive, so that an enclosed sealed space is created about the catheter at the skin puncture site. A needle access port is provided in the wall for filling the sealed chamber with antiseptic, withdrawing antiseptic for testing, or replenishing/changing the antiseptic as necessary. The second embodiment is of similar construction, except that a seam is provided in the side wall to facilitate placement or replacement without removal of the catheter. If desired, a purge vent can also be provided in the side wall of the sleeve.

BRIEF DESCRIPTION OF DRAWINGS

A better understanding of the invention can be had by reference to the following Detailed Description in conjunction with the accompanying Drawings, wherein.

DETAILED DESCRIPTION

Figure 1:
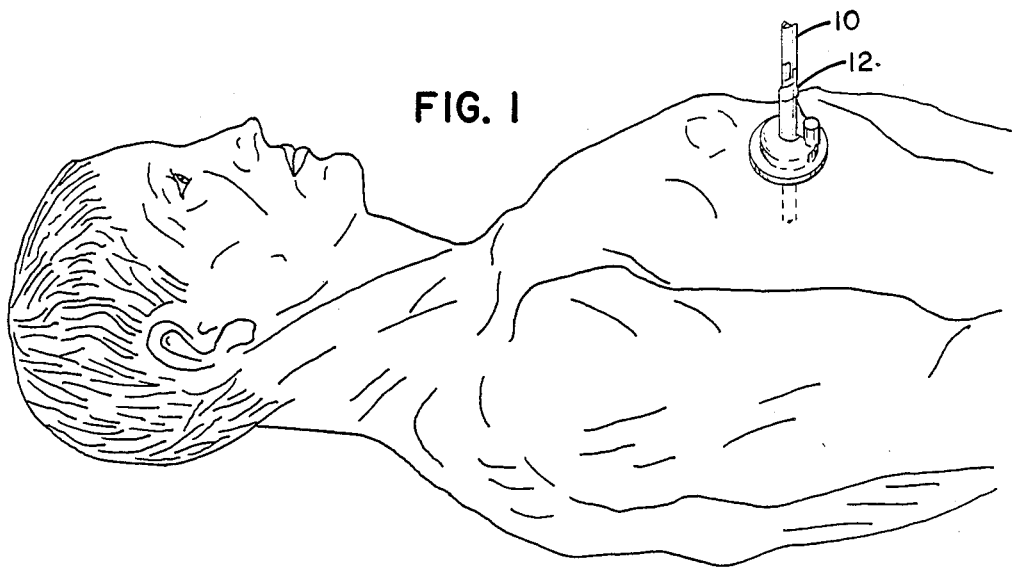
Fig. 1 is an illustration of a patient with an indwelling catheter secured in place with the protective catheter sleeve of the invention.

Referring now to the Drawings, wherein like reference numerals designate like or corresponding elements throughout the views, and particularly referring to FIG. 1, there is shown a patient including a transcutaneous, in-dwelling catheter 10 of the type used for administering nutrients or medication, assisting blood circulation, etc. The catheter 10 is stabilized and secured in place on the patients skin by the protective catheter sleeve 12 of the invention. Although the protective catheter sleeve 12 of the invention is particularly useful with catheters, it will be understood that the invention can also be used with other transcutaneous devices such as tubes or wires or any long-term device left in place up to 24 hours or more. As will be explained more fully hereinafter, the protective catheter sleeve 12 defines a continuous fluid seal at the junction between the catheter and the patient's skin in a manner which allows removal and replacement of antiseptic fluid as necessary to minimize infection, particularly during long-term patient care.

Figure 2:
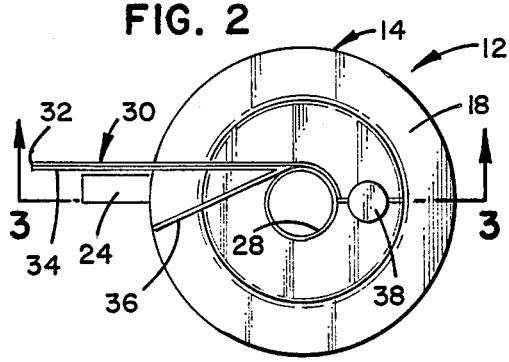
FIG. 2 is a top view of a protective catheter sleeve incorporating the first embodiment of the invention.
Figure 3:
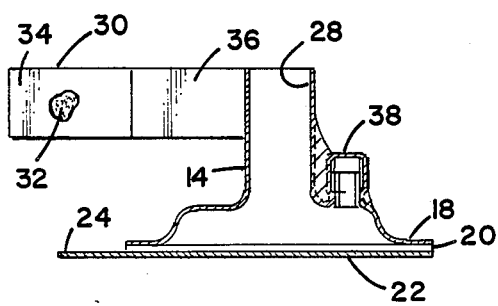
FIG. 3 is a cross-sectional view taken along lines 3—3 of FIG. 2 in the direction of the arrows.
Figure 4:
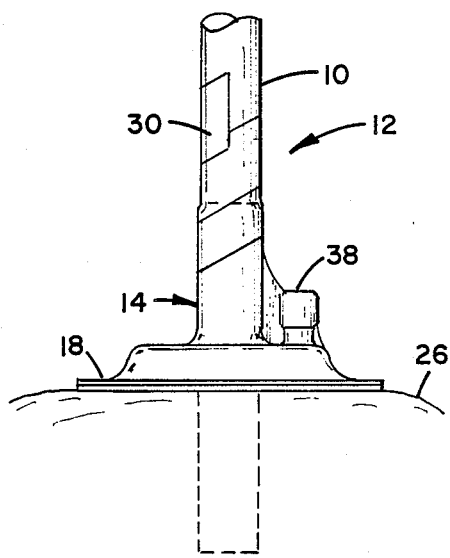
FIG. 4 is a side view of the protective catheter sleeve of the first embodiment.
Figure 5:
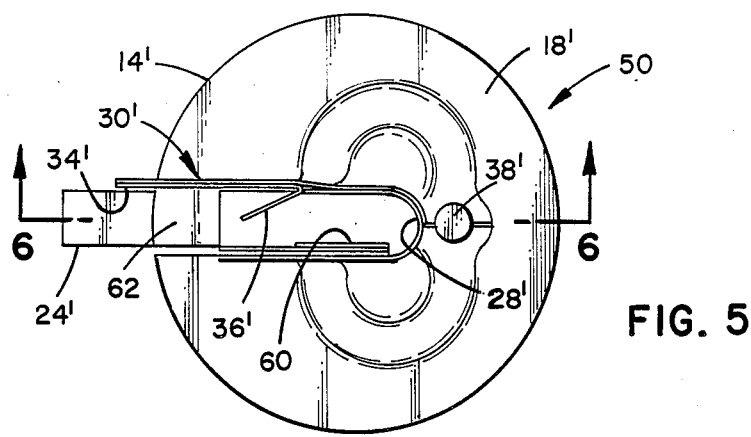
FIG. 5 is a top view of a protective catheter sleeve incorporating the second embodiment of the invention.
Figure 6:
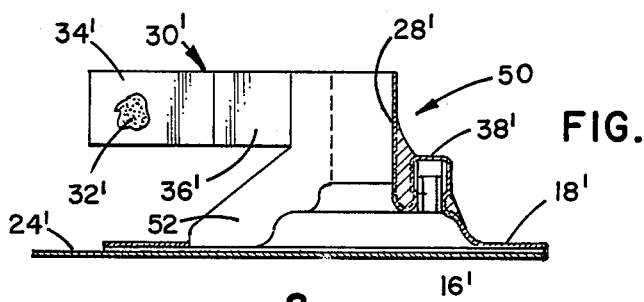
FIG. 6 is a cross-sectional view taken along lines 6—6 of FIG. 5 in the direction of the arrows.
Figure 7:
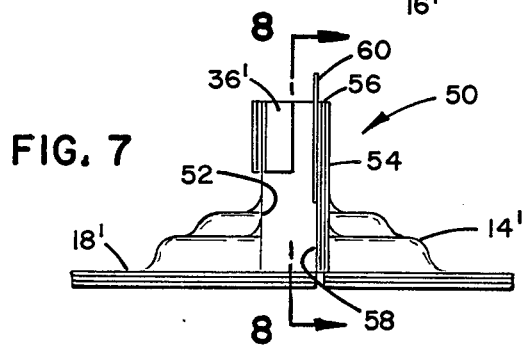
FIG. 7 is a side view of the protective catheter sleeve of the second embodiment.
Figure 8:
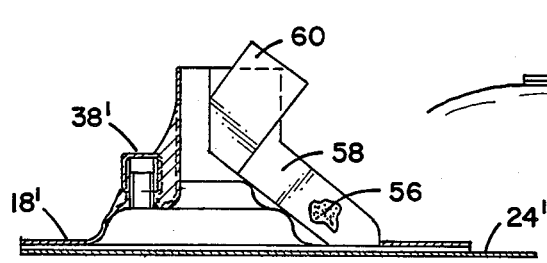
FIG. 8 is a cross-sectional view taken along lines 8—8 of FIG. 7 in the direction of the arrows.
Figure 9:
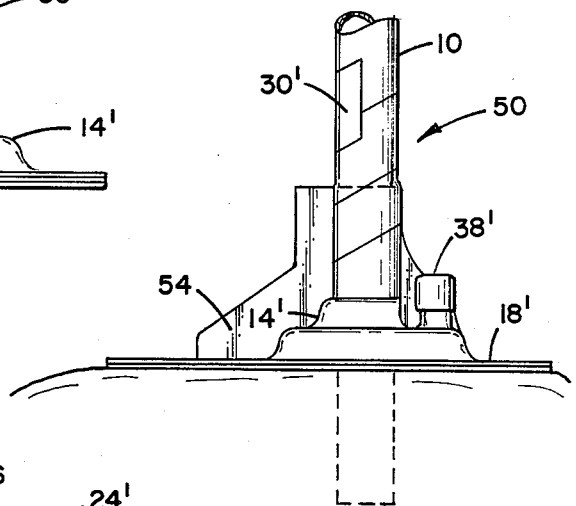
FIG. 9 is a side view of the protective catheter sleeve of the second embodiment secured about an in-dwelling catheter.

Referring now to FIGS. 2-4, there is shown the protective catheter sleeve 12 of the first embodiment. The sleeve 12 includes a flexible or resilient surrounding side wall 14 defining an internal chamber 16 of sufficient volume, such as 10 cc or less. The sleeve 14, which is preferably substantially transparent or translucent, is formed of suitable material, such as thermoformed urethane sheet of 0.005-0.020 inch thickness for strength flexibility and bio-compatibility. Polypropylene, polyethylene, polyurethane, or polyvinyl could also be used. The lower end of the side wall 14 includes a surrounding radial flange 18.

The underside of the flange 18 includes a layer of adhesive 20 covered by a removable liner 22. The adhesive 20 is preferably hypoallergenic skin adhesive of the acrylic or silicon-based type which is readily available from various commercial sources. In accordance with the preferred embodiment, a pull-tab 24 is provided on one side of the liner 22 in order to facilitate removal thereof and adhesive attachment to the skin 26 of the patient as shown in FIG. 4.

The upper end of the flexible side wall 14 includes an opening 28 for receiving the catheter 10, wire or other transcutaneous device. The upper end of the flexible side wall 14 is also adapted for releasable engagement with the catheter 10. As illustrated, a length of tape 30 having adhesive 32 on one side is secured at one end to the upper end of the side wall 14. The adhesive 32 on one side of tape 30 is covered by a releaseable liner 34 including a folded back pull-tab 36 which is located adjacent to the upper end of the side wall 14 so that the tape can be wrapped about the catheter 10 as the liner is stripped away in one motion.

Although the upper end of side wall 14 is illustrated and described as being adhesively secured to catheter 10, it will be understood that other suitable means of sealing attachment could be used.

The protective catheter sleeve 12 also includes a needle access port or injection site 38 in the side wall 14 in order to provide access to the sealed chamber therein for adding, withdrawing, or changing antiseptic fluid therein as necessary. The injection site 38 is of substantially conventional construction. For example, an injection adapter male slip like that available from Medex, Inc., of Hillard, Ohio, can be used.

The protective catheter sleeve 12 is used as follows. Before the catheter 10 is inserted transcutaneously into the vascular system of the patient, the sleeve 12 is slipped over the catheter, which is then inserted transcutaneously by needle stick or operation into the body. With the catheter 10 in place the sleeve 12 is slid toward the skin surrounding the puncture site or egress site of the catheter. The liner 24 is removed via pull-tab 24 to expose the adhesive 20 on the lower end of the sleeve side wall 14, which is then adhesively secured to the skin of the patient around the puncture site. After the sleeve 12 is attached to the skin the top end thereof is secured to the catheter 10. Suitable antiseptic solution is then injected into chamber 16 via port 38 so that the skin surrounding the puncture site as well as the immediate outside wall of the catheter 10 is continuously bathed with antiseptic solution in order to prevent or reduce the incidence of infection associated therewith. After the internal chamber 16 has been substantially filled with anticeptic solution, the tape 30 is wrapped about the catheter 10 as the liner 24 is stripped away via tab 36 in order to provide an adhesively secured, sealed connection between the catheter and the sleeve. Every few hours the antiseptic fluid within the device is aspirated via port 38 without disturbing the catheter 10 or the protective sleeve 12. The aspirated fluid can be cultured or analyzed; new and/or different antiseptic solution can then be injected.

If desired, additional strips of adhesive tape or a ring of adhesive tape (not shown) can be provided around the flange 18 of the protective catheter sleeve 12 for reinforcement.

Referring now to FIGS. 5-9, there is shown a protective catheter sleeve 50 incorporating a second embodiment of the invention herein. The sleeve 50 includes several component parts which are substantially identical in construction and function to corresponding parts of the sleeve 12 of the first embodiment. Accordingly, the same reference numerals have been used to identify such parts, but have been differentiated therefrom by means of prime(') notations.

The primary difference between the two embodiments comprises the fact that the protective catheter sleeve 50 of the second embodiment is of split construction to facilitate removal and replacement of the sleeve about an in-dwelling catheter 10 without disturbing the catheter. The sleeve 12 of the first embodiment is adapted primarily for placement in conjunction with the catheter 10. It is difficult to replace the sleeve 12 without removing or at least disturbing the catheter 10. The sleeve 50 of the second embodiment overcomes that disadvantage by including a seam defined by two longitudinal flanges 52 and 54 in the side wall 14'. The longitudinal flanges 52 and 54 are positioned opposite the needle access port 38'. A suitable adhesive 56 is provided on the inside surface of one of the longitudinal flanges 52 and 54, such as flange 54 as shown, with a releaseable liner 58 having a pull-tab 60 on one end thereof for exposing the adhesive prior to connection of the flanges. A tab 62 is provided on flange 18 for underlapping, sealed engagement with the opposite portion of the flange.

It will thus be appreciated that the protective catheter sleeve 50 can be positioned around an in-dwelling catheter 10 without disturbing the catheter, after which the liner 58 can be stripped away so that the longitudinal flanges 52 and 54 can be secured together to close the seam in the side wall 14'. The lower end of the sleeve 50 is then secured to the skin of the patient, followed by filling the internal chamber 16' with suitable anticeptic solution via port 38', and then securing the upper end of the sleeve to the catheter 10 as in the first embodiment.

From the foregoing, it will thus be apparent that the present invention comprises a protective catheter sleeve that serves as an antiseptic barrier against infection at the puncture site of a catheter, or other transcutaneous device. The antiseptic fluid within the protective sleeve can be sampled, replenished, or changed as necessary without disturbing the sleeve or the catheter. Other advantages will be evident to those skilled in the art.

Although particular embodiments of the invention have been illustrated in the accompanying Drawings, and described in the foregoing Detailed Description, it will be understood that the invention is not limited only to the embodiments disclosed, but is intended to embrace any equivalents, modifications and/or rearrangements of elements falling within the scope of the invention as defined by the following claims.

What is claimed is:

1. A protective catheter sleeve, comprising:
   a flexible boot having a surrounding side wall, a open bottom end, and an open top end for receiving the catheter therethrough;
   means for adhesively securing the bottom end of said boot about a catheter puncture site in the skin of a patient;
   means for securing the top end of said boot in sealing engagement about the catheter to define a chamber enclosing adjacent portions of the catheter and skin at the puncture site; and
   means defining a needle access port in the wall of said boot for selectively injecting and withdrawing antiseptic solution therein.

2. The protective catheter sleeve of claim 1, wherein said boot is constructed from a suitable bio-compatible material such as material selected from the group consisting of polyurethane, polypropylene, polyethylene, polyvinyl, and silicone rubber.

3. The protective catheter sleeve of claim 1, wherein said means for adhesively securing the bottom end of said boot comprises a layer of non-allergic, non-irritant adhesive, and a releaseable liner for selectively exposing the adhesive prior to contact with the skin of the patient.

4. The protective catheter sleeve of claim 1, wherein the lower end of said boot is generally divergent and the upper end thereof is generally convergent.

5. The protective catheter sleeve of claim 1, wherein said means for securing the top end of said boot to said catheter comprises adhesive.

6. The protective catheter sleeve of claim 1, wherein the side wall of said boot includes a seam extending between the top and bottom ends, and further including:
   means for securing the seam in sealed engagement.

7. The protective catheter sleeve according to claim 6, wherein the sleeve is located generally opposite said needle access port means.

8. The protective catheter sleeve of claim 1, wherein the bottom end of the wall of said boot includes an integral radially extending flange.

9. A protective catheter sleeve, comprising:
   a flexible boot having a surrounding side wall, a divergent open bottom end with a radial flange, and a convergent open top end for receiving the catheter therethrough;
   the side wall, top and bottom ends of said boot being of integral construction;
   means for adhesively securing the flange of the bottom end of said boot about a catheter puncture site in the skin of a patient;
   means for adhesively securing the top end of said boot in sealing engagement about the catheter to define a chamber enclosing adjacent portions of the catheter and skin at the puncture site; and
   means defining a needle access port in the wall of said boot for selectively injecting and withdrawing antiseptic solution therein.

10. The protective catheter sleeve of claim 9, wherein said boot is constructed from a suitable bio-compatible material such as material selected from the group consisting of polyurethane, polypropylene, polyethylene, polyvinyl, and silicone rubber.

11. The protective catheter sleeve of claim 9, wherein said means for adhesively securing the bottom end of said boot comprises a layer of non-allergic, non-irritant adhesive, and further including:
   a releaseable liner for selectively exposing the adhesive prior to contact with the skin of the patient.

12. The protective catheter sleeve of claim 9, wherein the volume of the chamber defined therein is 10 cc or less.

13. A protective catheter sleeve, comprising:
- a flexible boot having a surrounding side wall, a divergent open bottom end with a radial flange, and a convergent open top end for receiving the catheter therethrough;
- the side wall, top and bottom ends of said boot being of integral construction;
- means for adhesively securing the flange of the bottom end of said boot about a catheter puncture site in the skin of a patient;
- means for adhesively securing the top end of said boot in sealing engagement about the catheter to define a chamber enclosing adjacent portions of the catheter and skin at the puncture site;
- the side wall of said boot including a seam extending between the top and bottom ends to facilitate removal and replacement about an in-dwelling catheter;
- means for securing the side wall seam in sealed engagement; and
- means defining a needle access port in the wall of said boot for selectively injecting and withdrawing antiseptic solution therein.

14. The protective catheter sleeve of claim 13, wherein said boot is constructed from a suitable biocompatible material such as material selected from the group consisting of polyurethane, polypropylene, polyethylene, polyvinyl, and silicone rubber.

15. The protective catheter sleeve of claim 13, wherein said means for adhesively securing the bottom end of said boot comprises a layer of non-allergic, non-irritant adhesive, and further including:
- a releaseable liner for selectively exposing the adhesive prior to contact with the skin of the patient.

16. The protective catheter sleeve of claim 13, wherein the side wall seam is located generally opposite said needle access port means.

17. The protective catheter sleeve of claim 13, wherein the volume of the chamber defined therein is 10 cc or less.

* * * * *